United States Patent [19]
Adams

[11] Patent Number: 5,693,023
[45] Date of Patent: Dec. 2, 1997

US005693023A

[54] SYRINGE WITH RETRACTABLE NEEDLE ASSEMBLY

[75] Inventor: Robert D. Adams, Shamong, N.J.

[73] Assignee: Adventec, Inc., Medford, N.J.

[21] Appl. No.: 749,997

[22] Filed: Nov. 15, 1996

[51] Int. Cl.$^6$ ............................................. A61M 5/00
[52] U.S. Cl. ............................... 604/195; 604/110
[58] Field of Search ......................... 604/195, 192, 604/110, 198, 263

[56] References Cited

U.S. PATENT DOCUMENTS

| | | | |
|---|---|---|---|
| 4,838,869 | 6/1989 | Allard | 604/195 |
| 4,874,382 | 10/1989 | Lindemann et al. | 604/195 |
| 4,917,679 | 4/1990 | Kronner | 604/198 |
| 4,955,870 | 9/1990 | Riderheim et al. | 604/195 |
| 5,190,526 | 3/1993 | Murray et al. | 604/110 |
| 5,209,739 | 5/1993 | Talalay | 604/195 |
| 5,267,961 | 12/1993 | Shaw | 604/110 |
| 5,338,304 | 8/1994 | Adams | 604/110 |
| 5,395,337 | 3/1995 | Clemens et al. | 604/110 |

FOREIGN PATENT DOCUMENTS

0480862  4/1992  European Pat. Off. .

*Primary Examiner*—John D. Yasko
*Attorney, Agent, or Firm*—Volpe and Koenig, P.C.

[57] ABSTRACT

An improved syringe of the type having a hollow body which is closed at one end by an injection means and is open at the other end, the open end receives an elongated plunger means which moves through the hollow body and forces the contents of the body through the injection means. The improvement is comprised of an elastic member which retracts the injection means into a protective covering.

18 Claims, 8 Drawing Sheets

SYRINGE WITH RETRACTABLE NEEDLE ASSEMBLY

BACKGROUND OF THE INVENTION

1. Field of the Invention

The present invention relates generally to protection against an accidental sharps injury or stick from an unprotected needle. More particularly, the present invention relates to a retractable needle syringe for protection from an accidental sharps injury or stick from a used needle of the type commonly associated with medical practice. Most particularly, the present invention relates to an automatic retractable needle syringe for protection against an accidental sharps injury or sticks from a used syringe.

2. Description of the Related Art

For some time, the art has recognized the desirability of protecting personnel from accidental sharps injuries or needle sticks. More recently, concerns have been expressed about the possibility of transmitting serious or potentially fatal infection as a result of such accidents. Most recently, the Occupation Safety and Health Administration has issued guidelines which are generally known as Standard 1910.1030. Although, the art has recognized the desirability of protecting against accidental sharps injury or needle sticks, it is believed that practical protective devices are still not available.

U.S. Pat. No. 5,209,739 discloses a hypodermic assembly and a syringe, both having a retractable elastomeric tube is connected between the cannula to the fluid chamber. In each of the embodiments, a separate mechanical device must be independently operated by the user to cause retraction of the cannula into a second compartment. Since the fluid must travel through the elastomeric tube to bypass the second compartment, there is a potential risk of injecting air directly into the patient if the elastomeric tube breaks.

European Patent No. 0 862 A1 discloses a device in which a needle is retracted into the syringe. In several of the embodiments, the device requires the user to independently operate a mechanical device to cause retraction of the needle. In the one embodiment which utilizes an elastic member, the elastic member is not preloaded and requires the user to depress the plunger to load the elastic member and thereafter continue to apply pressure on the plunger to avoid premature withdrawal of the plunger. As such, the device requires two hands for its operation.

U.S. Pat. Nos. 5,395,337, 5,267,961, 5,190,526, 4,955,870, 4,874,382 and 4,838,869 each disclose a device in which the needle is retracted by a compressive spring. In each of the devices, the spring and needle are connected by a separate member which passes through the sealing member of the plunger. This requires additional sealing means between the separate member and the plunger sealing member.

Accordingly, there is a need for a syringe having an automatically retracted used needle assembly that can be used in a conventional manner and does not require elaborate manufacturing or sealing means.

SUMMARY OF THE INVENTION

The present invention overcomes the difficulties discussed above by providing an automatically retracting single use syringe that includes a hollow body which is substantially open at one end and is substantially closed at its other end except for injection means aperture. The injection means extends from one side of a needle assembly which has a geometric configuration at its other side. An elongated plunger moves in the hollow body and has retainer means spaced between its ends. One end of the plunger has a geometric configuration which is matable with the needle assembly geometric configuration. A preloaded elastic member is attached to the plunger retainer means. One end of the elastic member includes means for automatically releasing the elastic member from a retainer means upon substantial mating of the geometric configurations so that the relaxing elastic member draws the injection means into the hollow body.

DETAILED DESCRIPTION OF THE PREFERRED EMBODIMENTS

The preferred embodiments will be described with reference to drawing figures where the numerals represent like elements throughout.

Figure 1:
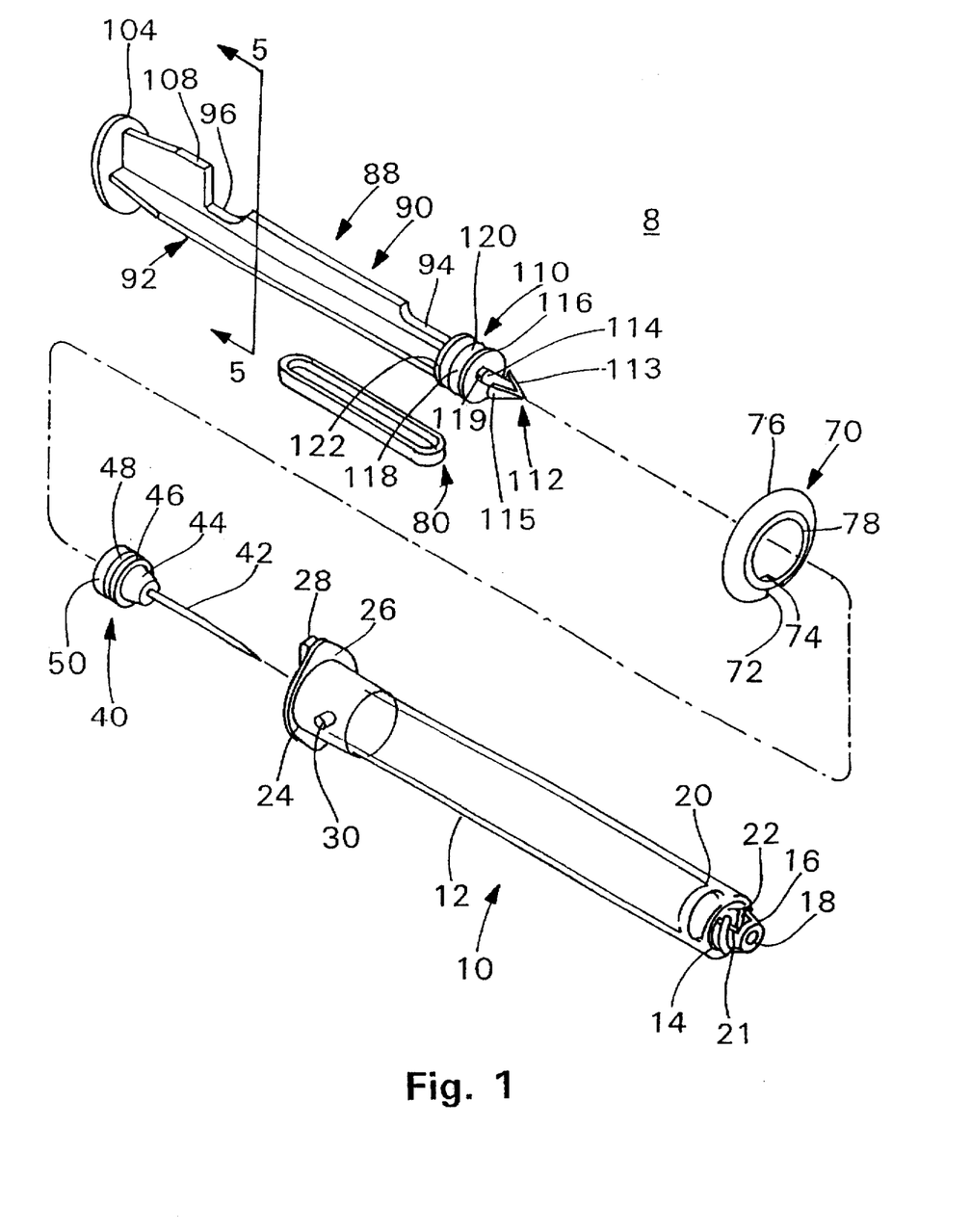
FIG. 1 is an exploded view of a syringe assembly in accordance with the present invention.

With reference to FIG. 1, the components of the preferred embodiment 8 of the invention will be described. The preferred embodiment 8 is comprised generally of the syringe 10, the needle assembly 40, the automatic release member 70, the elastic member 80 and the plunger assembly 88.

Figure 13:
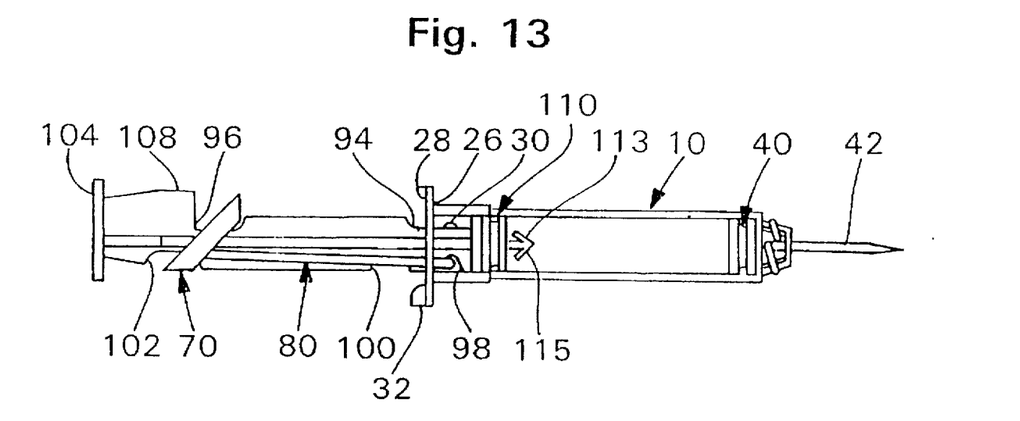
FIG. 13 depicts the syringe of FIG. 12 after the syringe has been rotated.

The syringe 10 is comprised of a hollow body portion 12 which has a closed end 14 and an open end 24 surrounded by a grip ring 26. Integral with grip ring 26 are a stop 28 and a guiding shoulder 32 which is shown in FIG. 13. On the interior of the hollow body 12, adjacent the open end 24, is a pin 30.

The closed end 14 is defined by a truncated cone 16 which includes a truncating plane having an aperture 18. On the interior of the hollow body 12, at a position adjacent to the closed end 14, is a retaining ring 20 that retains the needle assembly 40 in position during use. Alternatively, retaining ring 20 may be replaced by a plurality of projections.

The needle assembly 40 is comprised of a needle 42 which is centrally positioned in the conical projection 44. The conical projection 44 generally compliments the interior of the truncated cone 16 in the syringe 10. However, the interior surface of the truncated cone 16 has a number of ridges 21 which extend from the closed end 14 to the truncating plane of the cone 16. These ridges 21 act to simplify the breaking of the seal between the needle assembly 40 and the interior surface of cone 16, thereby reducing the resistance which must be overcome to withdraw the needle assembly 40.

Figure 2:
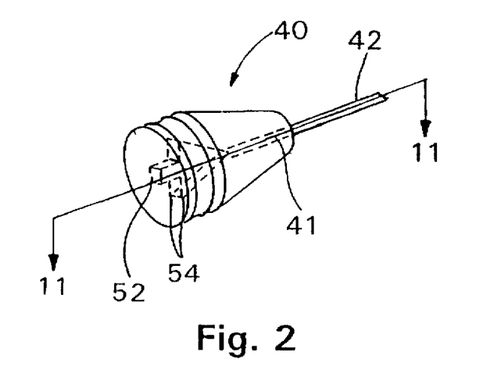
FIG. 2 depicts the needle assembly.

Immediately adjacent to the projection 44 is a resilient collar 46. Immediately behind the collar 46 is the angular recess 48. Adjacent to the recess 48 is the sealing ring 50. The resilient collar 46, the angular recess 48 and the sealing ring 50 are all formed as a unitary molding of synthetic rubber. The interior recess 41 of needle assembly 40 communicates with the hollow needle 42. Along the rear surface of the needle assembly is a rectangularly configured cavity 52 which is shown in detail in FIG. 2. In the preferred embodiment, the cavity 52 is shaped like an arrow head with narrowly spaced walls 54 defining the shorter side of the rectangle.

Automatic release member 70 holds the elastic member 80 on the plunger member 88 in a preloaded or tensioned condition until the plunger member 88 is completely depressed. In the preferred embodiment, the elastic member 80 is an elastic band which is approved for medical uses. The plunger assembly 88, the elastic member 80, and the automatic release 70 will be described in greater detail with reference to FIGS. 3-7.

Figure 3:
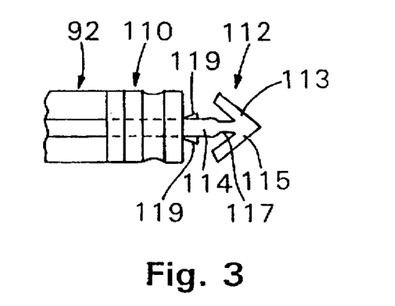
FIG. 3 depicts the tip end of the plunger assembly.

The plunger assembly 88 includes a plunger portion 90 and a sealing member 110. The plunger portion 90 has a shaft 92 which terminates at one end in the force application pad 104 and at its other end in geometrically configured tip 112. As shown in FIG. 3, geometrically configured tip 112 is arrow shaped with two collapsible fins 113, 115 as rod 114 extends from the end of the shaft 92. At the tip of rod 114 are detents 117 which allow each fin 113, 115 to collapse against the rod 114. The base of rod 114 has two ramps 119 which assist in withdrawing tip 112 from the needle assembly cavity 52 which is in its initial position. A sealing member 110 is placed on the rod 114 in sealing engagement therewith. A suitable sealing member 110 is described in detail in my U.S. Pat. No. 5,338,304, which description is incorporated herein by reference.

Figure 4:
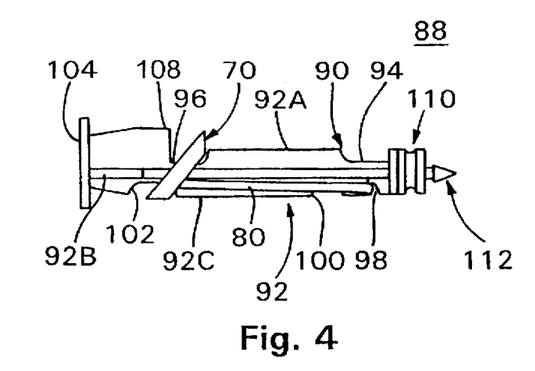
FIG. 4 is a side elevation of the plunger assembly.
Figure 5:
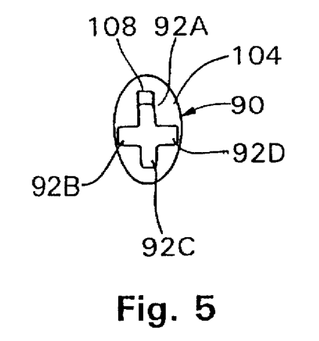
FIG. 5 is a cross sectional view of the plunger assembly taken along line 5—5 of FIG. 1.

As shown in FIGS. 4–5, the shaft 92 consists of 4 ribs 92A, 92B, 92C, 92D formed in a substantially cross shape with angular channels formed between adjacent ribs. The upper rib 92A has a rotation notch 94 adjacent the sealing member 110 and a first retaining notch 106 adjacent the force applicator pad 104. The lower rib 92C has a second retaining notch 102 adjacent the force applicator pad 104, a third retaining notch 98 adjacent the sealing member 110, and a locking notch 100 therebetween.

The automatic release member 70 is placed on the plunger shaft 92 with its upper portion located in the first retaining notch 96 and its lower portion in the second retaining notch 102. The elastic member 80 is attached at one end to the automatic release member 70 and at the other end to the third retaining notch 98. The second retaining notch 102 and the third retaining notch 98 are spaced so that the elastic member 80 is preloaded, i.e. there is tension in the elastic member 80. The automatic release member 70 is held in the second retaining notch 102 by the tensioned elastic member 80. When the lower portion of the automatic release member 70 is held in the second retaining notch 102, the upper portion is at an approximately 45 degree angle from the lower portion and is unrestrained in the first retaining notch 96.

Figure 6:
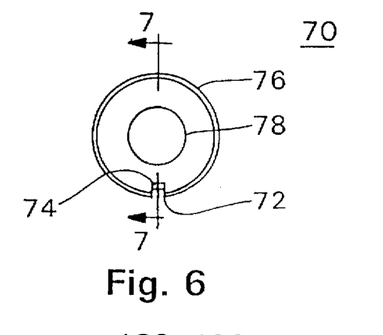
FIG. 6 is a front elevational view of the automatic release member.
Figure 7:
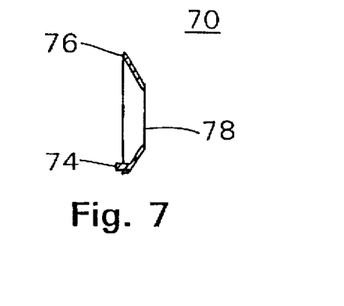
FIG. 7 is a cross sectional view of the automatic release member taken along line 7—7 of FIG. 6.

As shown in FIGS. 6 and 7, the automatic release member 70 is generally a beveled ring. The small opening 78 is large enough to allow the automatic release member 70 to pass along the plunger assembly 88 until it reaches the trailing edge 108 of the first retaining notch 96. The trailing edge 108 fits into the large opening 76, but will not pass through the small opening 78. The lower portion of the automatic release member 70 has a notch 72 and a projection 74. The elastic member 80 is passed through notch 72 and is hooked or secured to the projection 74. The automatic release member 70 is then positioned on the plunger assembly 88 as previously described above.

Figure 8:
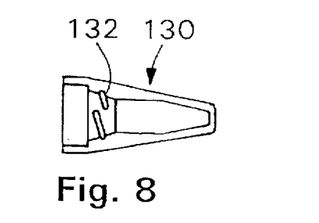
FIG. 8 shows a side elevation of a protective cap which may be used with the syringe.
Figure 9:
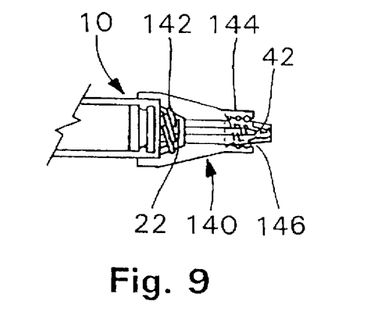
FIG. 9 depicts a Luer-lock adapter attached to the syringe.

FIG. 8 shows a protective cap 130 with threads 132 which may be used with the device 8. In the preferred embodiment, the exterior surface of truncated cone 16 has threads 22 which allow the syringe 10 to be connected to the threaded cap 130 and other equipment which uses a standard Luer-lock connection. FIG. 9 shows a Luer-lock adapter 140 with threads 142 which mate with the threads 22 on the syringe 10. The opposite end of the adapter 140 has a second set of threads 144 and a membrane 146 which covers the end of the adapter 140 to keep it sanitary. To utilize the device 8 with an intravenous line, the adapter 140 is connected to the closed end 14 of the syringe 10. As the adapter 140 is connected to the syringe 10, the needle 42 punctures the membrane 146 and extends slightly past the end of the adapter 140. The second set of threads 144 can than be used to connect the device to an intravenous line. Apart from connection to a Luer-lock rather then direct injection into the patient, the device 8 operates as described hereinafter.

Having described the components of the preferred embodiment 8, its operation will be described in more detail with reference to FIGS. 10–20.

Figure 10:
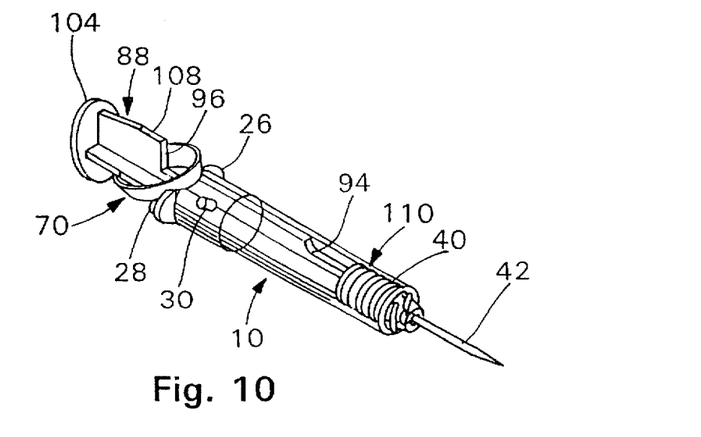
FIG. 10 depicts the syringe of FIG. 1 in an assembled but unused condition.
Figure 11:
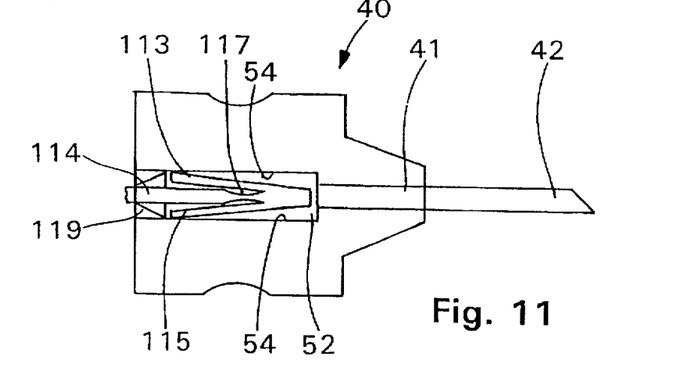
FIG. 11 is an expanded view of the cross section of the needle assembly taken along line 11—11 of FIG. 2, with the tip of the plunger inserted therein.

FIG. 10 shows the device 8 when it is first removed from its packaging and the protective cap 130 is removed. The plunger assembly 88 is aligned within the syringe 10 such that the pin 30 is positioned in the groove between the upper rib 92A and the left rib 92B. The plunger assembly 88 is in a first alignment in which the fins 113, 115 are horizontal and therefore are collapsed by the vertical walls 54 of the cavity 52 as shown in FIG. 11. This alignment keeps the tip 112 from locking with the needle assembly 40. The ramps 119 help prevent the collapsed fins 113, 115 from catching on the walls 54 of the cavity.

Figure 12:
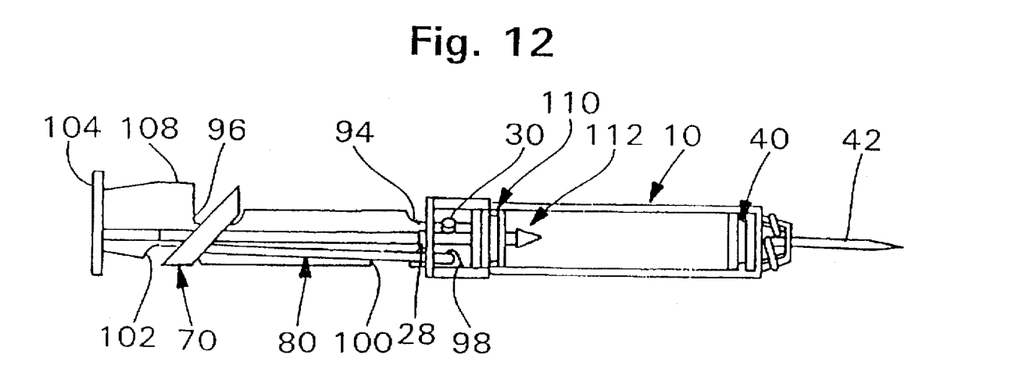
FIG. 12 depicts the syringe of FIG. 10 after the plunger assembly has been withdrawn.

The plunger assembly 88 is then withdrawn to the position shown in FIG. 12 to fill the hollow body 12 in a conventional manner. It will be noted that in the withdrawn position, the elastic member 80 remains in a preloaded position. Since the elastic member 80 is tensioned between two points on the plunger, the elastic member 80 does not act to withdraw or depress the plunger assembly 88. With the plunger assembly 88 withdrawn sufficiently, the pin 30 is aligned with the rotation notch 94. As shown in FIG. 13, syringe 10 and plunger assembly 88 can then be rotated relative to each other so that the fins 113, 115 are in alignment with the narrowly spaced walls 54 of the cavity 52.

Once the air has been purged from the syringe 10 in a known manner, the device 8 is ready for injection of the needle 42 into the patient. As stated above, the elastic member 80 is not acting to move the plunger assembly 88 in either direction. Therefore, the user is free to hold the device 8 in the traditional dart like fashion between their thumb and forefinger of one hand, and use the other hand to pinch the patient's skin at the point of insertion for subcutaneous injection, spread the skin for intermuscular injection, and stabilize the skin for IV injection. These methods of injection are the generally preferred methods in the medical field. Once the user has inserted the needle 42 into the patient, the user injects the substance into the patient by depressing the force application pad 104.

Figure 14:
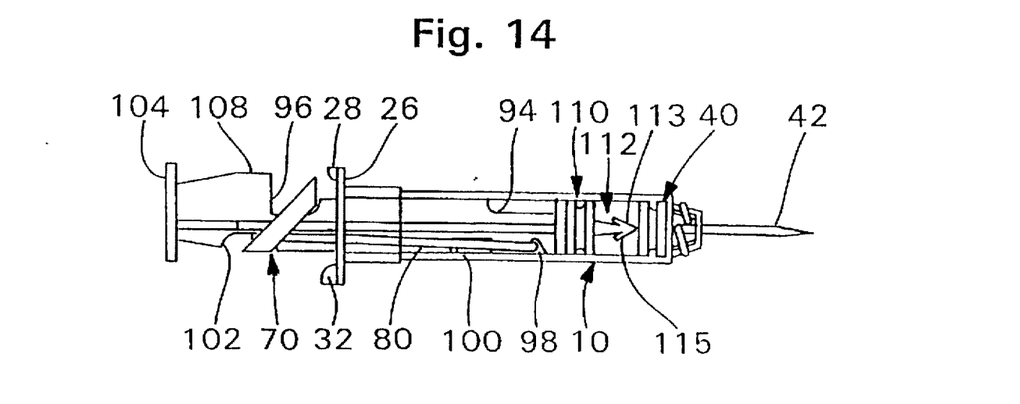
FIG. 14 depicts the syringe of FIG. 13 as the sealing member begins to connect with the needle assembly.

As shown in FIG. 14, as the geometrically configured tip begins to pass into the needle assembly 40, the upper portion of the automatic release member 70 is about to contact the finger grip 26 and the stop 28. Slightly thereafter, the upper portion of the automatic release member 70 contacts the finger grip 26 and the stop 28 and begins to move upward on the stop 28 as shown in FIG. 15.

Figure 15:
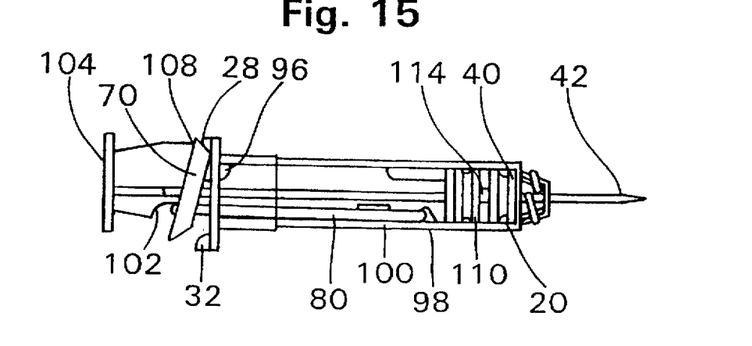
FIG. 15 depicts the syringe of FIG. 14 upon substantial depression of the plunger assembly.
Figure 16:
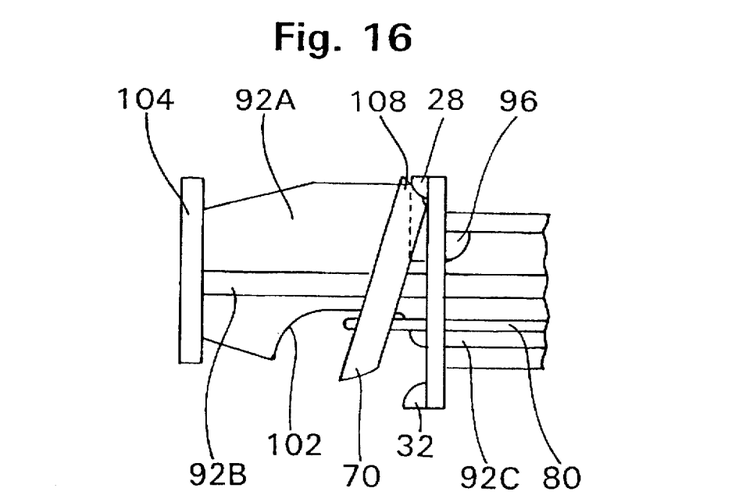
FIG. 16 depicts an expanded view of the rear portion of the syringe shown in FIG. 15.

FIG. 16, which is an expanded view of the rear of the device 8 in the position of FIG. 15, shows the trailing edge 108 of the first retaining notch 96 pinching the automatic release member 70 between itself and the stop 28. The continuing force as the plunger assembly 88 is completely depressed and the pinching of the automatic release member 70 between the trailing edge 108 and the stop 28 causes the lower portion of the automatic release member 70 to move down and backward, thereby automatically releasing from the second retaining notch 102 as depression of the plunger assembly 88 is completed.

Figure 17:
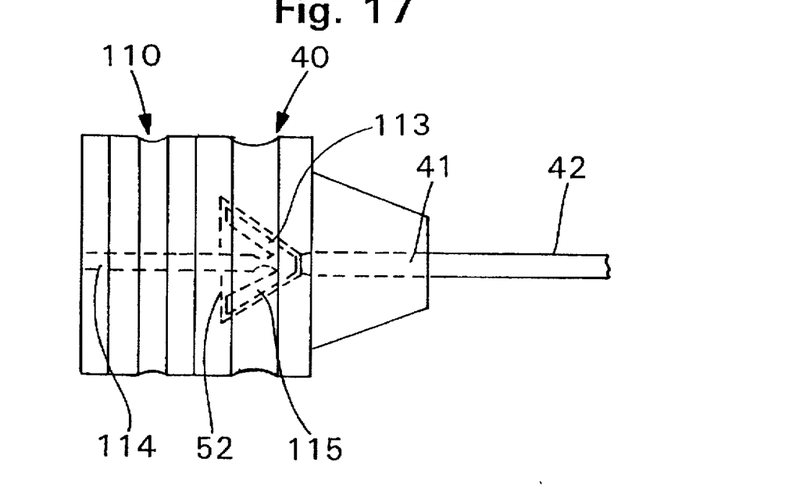
FIG. 17 depicts an expanded view of the mated needle assembly and plunger tip of FIG. 16.

As explained earlier, the fins 113, 115 of the tip 112 are now aligned with the longer sides of the rectangular cavity 52. The fins 113, 115 collapse as the tip 112 passes into the cavity 52, but upon complete depression of the plunger assembly 88, open inside the cavity 52 as shown in FIG. 17, thereby locking the plunger assembly together with the needle assembly 40. The notch 96 in plunger assembly 88 is of sufficient length so plunger 88 can be depressed slightly further to account for any possible compression between the needle assembly 40 and the sealing member 110 and to ensure that the components mate and that all of the fluid has been discharged from the syringe 10.

Figure 18:
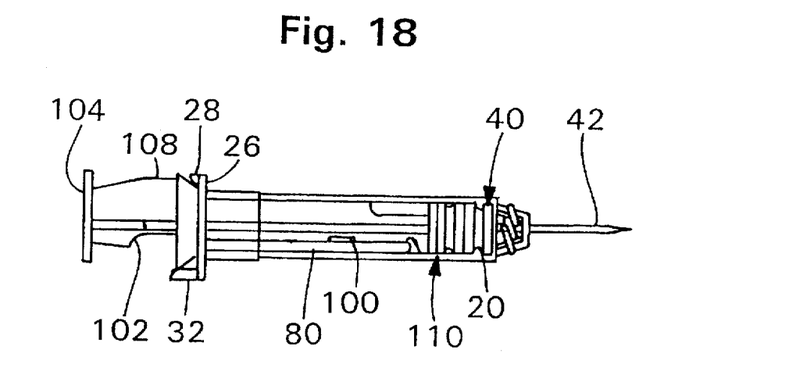
FIG. 18 depicts the syringe of FIG. 16 immediately after complete depression of the plunger assembly.
Figure 19:
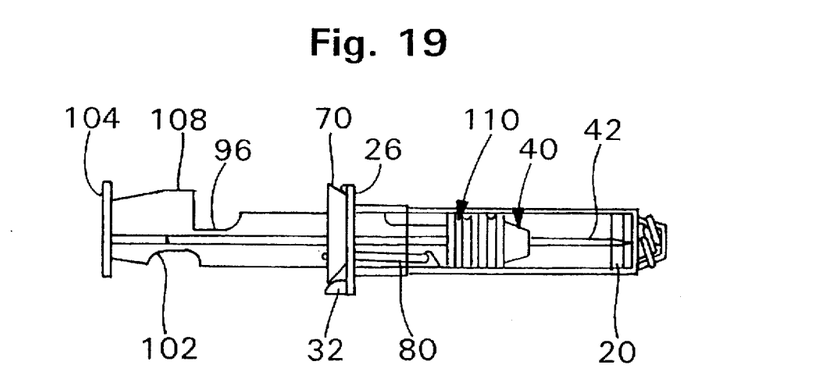
FIG. 19 depicts the syringe of FIG. 18 after it has been used and the needle has been retracted.
Figure 20:
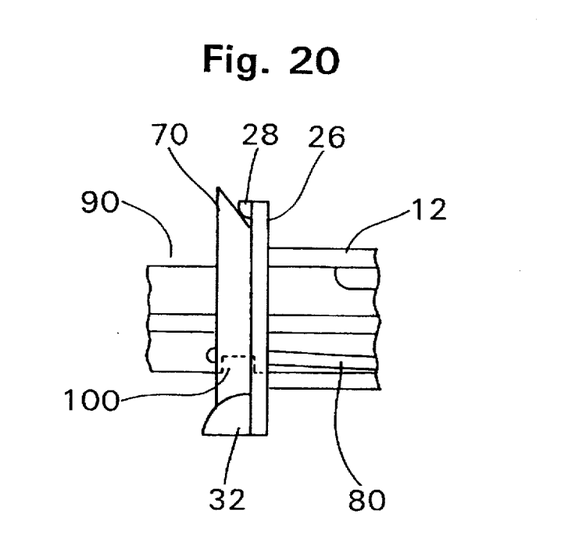
FIG. 20 depicts an expanded view of the rear portion of the syringe shown in FIG. 12.

As the automatic release member 70 releases, the plunger assembly 88 recoils slightly and guiding shoulder 32 urges the automatic release member 70 upward until it sits against the open end 14 of the syringe and the grip ring 26 as shown in FIG. 18. Since the elastic member 80 is now tensioned between a forward point on the plunger assembly 88, and a fixed point which is separate from the plunger assembly 88 and rear of the first point, the elastic member 80 retracts the plunger assembly 88 until the entire needle 42 is retracted within the syringe 10 as shown in FIG. 19. Once the plunger assembly 88 has been completely retracted, the guiding shoulder 32 continues to urge the automatic release member 70 inwardly until it locks into locking notch 100 as shown in FIG. 20. At this point, the plunger assembly 88 is secured so that it cannot be accidentally withdrawn from the syringe 10 or pushed so the needle projects from the syringe and so that the device 8 cannot be reused.

Figure 21:
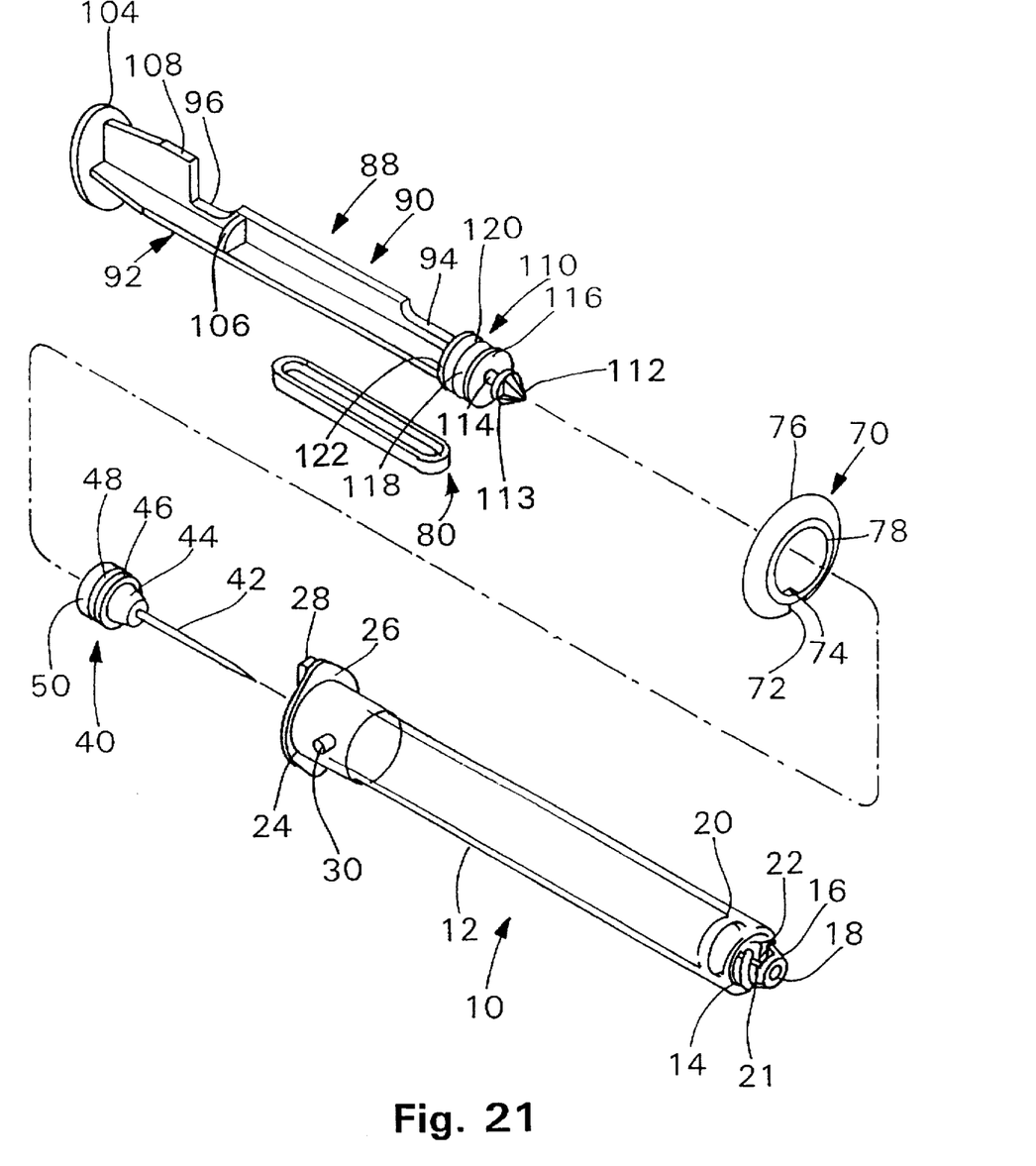
FIG. 21 is an exploded view of a second embodiment of the present invention.
Figure 22:
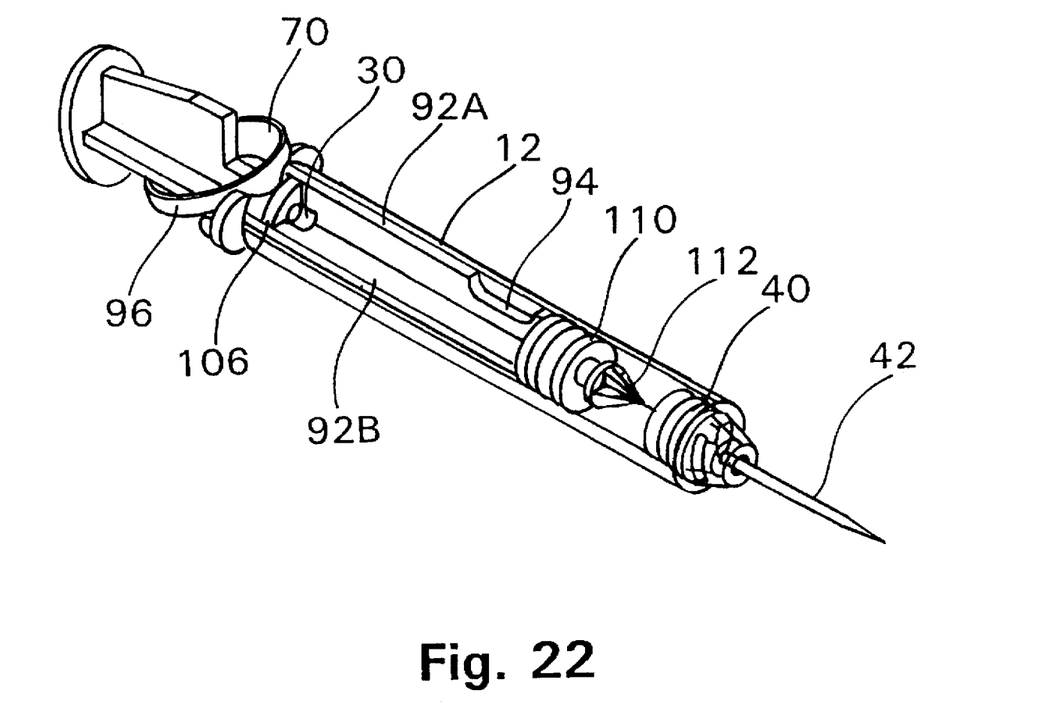
FIG. 22 depicts the syringe of FIG. 21 in an assembled but unused condition.

Now with reference to FIGS. 21–22, a second embodiment of the device 208 will be described. The components of the device 208 are generally the same as in the preferred embodiment, however, the tip 112 and cavity 52 have different configurations, and there is an abutment 106 formed between upper rib 92A and left rib 92B. The tip 112 is configured to have a plurality of fins 213 or alternatively, is shaped as a hemisphere as described in my earlier referenced U.S. Pat. No. 5,338,304, which description is incorporated herein by reference. The cavity 52 is shaped to compliment each tip 112 configuration respectively.

Operation of the device 208, is generally the same as operation of the preferred embodiment. However, since the tip 112 does not have a locking and a non-locking alignment, abutment 106, is provided to prevent premature mating of the plunger tip 112 and the cavity 52. As shown in FIG. 22, the plunger is initially aligned in the syringe such that abutment 106 contacts the pin 30, thereby preventing complete depression of the plunger assembly 88 and premature meeting of the tip 112 and the needle assembly 40. The device is then filled as in the preferred embodiment. The syringe is then again rotated such that the pin 30 passes through notch 94 until the pin 30 is aligned in the groove between upper rib 92A and right rib 92D. Since there is no abutment in this groove, the syringe can now be completely depressed. As the device 8 in the preferred embodiment is rotated in the same manner, an abutment 106 could be included in the preferred embodiment between upper rib 92A and left rib 92B to ensure that the tip 12 and needle assembly 40 do not prematurely mate.

Operation of the automatic release member 70 and retraction of the needle assembly 40 then proceeds as described for the preferred embodiment.

While the present invention has been described in terms of the preferred embodiments, other variations which are within the scope of the invention as defined in the claims will be apparent to those skilled in the art.

I claim:

1. A disposable, single use syringe comprised of:
   a hollow body which is substantially open at one end and is substantially closed at its other end except for an aperture through which an injection means passes;
   a retractable needle assembly positioned in the hollow body with the injection means passing through the aperture;
   an elongated plunger which moves in the hollow body and has spaced apart retainer means and means for retracting the needle assembly; and
   a preloaded elastic member having first and second ends for attachment to the retainer means; one end of the elastic member includes means for automatically releasing the elastic member from one retainer means upon substantial completion of the injection so that the relaxing elastic member draws the injection means into the hollow body.

2. The syringe of claim 1 wherein the means for retracting the needle assembly includes a first geometric configuration integral with the needle assembly and a second geometric configuration integral with the plunger.

3. The syringe of claim 2 wherein in a first orientation the geometric configurations unite without mating and in a second orientation the geometric configurations mate when united.

4. The syringe of claim 1 wherein the automatic release is a beveled ring.

5. The syringe of claim 1 wherein the needle assembly has a sealing ring which establishes a liquid tight seal against the interior of the hollow body.

6. The syringe of claim 1 wherein the needle assembly is formed as a unitary molding of synthetic material.

7. The syringe of claim 2 wherein the plunger assembly has a stroke of sufficient length to ensure complete mating of the geometric configurations upon discharge of the hollow body.

8. A disposable, single use syringe comprised of:
a hollow body which is substantially open at one end and is substantially closed at its other end except for an aperture through which an injection means passes;
a needle assembly, having the injection means extending from a first side and a geometric configuration at an opposite second side, is positioned in the hollow body with the injection means passing through the aperture;
an elongated plunger which moves in the hollow body and has spaced apart ends with first and second retainer means spaced therebetween; one plunger end has a complementary geometric configuration which mates with the needle assembly geometric configuration; and
a preloaded elastic member having a first end attached to the first retainer means and a second end attached to the second retainer means; the second end of the elastic member includes means for automatically releasing the second end of the elastic member from the second retainer means upon substantial mating of the geometric configurations so that the relaxing elastic member draws the injection means into the hollow body.

9. The syringe of claim 8 wherein in a first orientation the geometric configurations are unitable without mating and in a second orientation the geometric configurations mate when united.

10. The syringe of claim 9 wherein the substantially open end of the hollow body has a grip ring integral therewith, which grip ring has an integral stop and wherein the means for automatically releasing the second end of the elastic member includes a beveled ring to which the second end of the elastic member is attached, whereby pinching of the beveled ring between the stop and a portion of the plunger causes the beveled ring to automatically release from the second retainer means.

11. The syringe of claim 8 wherein the elongated plunger has a body portion which includes four ribs integrally formed in a substantially cross shape.

12. The syringe of claim 11 wherein the body is further characterized by a stopper projecting from an inside surface of the body adjacent the substantially closed end.

13. The syringe of claim 12 wherein a plunger rib has a notch defined therein adjacent to the geometric configuration end and of sufficient size to allow the stopper to pass therethrough such that the hollow body to be rotated relative to the plunger.

14. The syringe of claim 13 wherein an abutment is formed between two adjacent ribs.

15. The syringe of claim 14 wherein the plunger is initially aligned within the hollow body such that the abutment contacts the stopper.

16. The syringe of claim 8 wherein one geometric configuration is a collapsible arrow head and the other geometric configuration is a complementary cavity.

17. The syringe of claim 8 wherein the needle assembly has a sealing ring which establishes a liquid tight seal against the interior of the hollow body.

18. The syringe of claim 8 wherein the needle assembly is formed as a unitary molding of synthetic material.

* * * * *

UNITED STATES PATENT AND TRADEMARK OFFICE
CERTIFICATE OF CORRECTION

PATENT NO. : 5,693,023
DATED : December 2, 1997
INVENTOR(S) : Robert D. Adams

It is certified that error appears in the above-identified patent and that said Letters Patent is hereby corrected as shown below:

At column 1, line 28, insert --needle-- after the word "hypodermic".

At column 1, line 29, insert --cannula. An-- after the word "retractable".

At column 1, line 30, insert --and the passage-- after the word "cannula".

At column 5, line 26, insert --112-- after the word "tip".

At column 6, line 34, delete "12" and insert --112-- therefor.

Signed and Sealed this

Twenty-fourth Day of February, 1998

Attest:

BRUCE LEHMAN

Attesting Officer        Commissioner of Patents and Trademarks